(12) United States Patent
Antrim et al.

(10) Patent No.: US 7,091,335 B2
(45) Date of Patent: *Aug. 15, 2006

(54) DERIVATIZED REDUCED MALTO-OLIGOSACCHARIDES

(75) Inventors: Richard L. Antrim, Solon, IA (US); Frank W. Barresi, Coralville, IA (US)

(73) Assignee: Grain Processing Corporation, Muscatine, IA (US)

( * ) Notice: Subject to any disclaimer, the term of this patent is extended or adjusted under 35 U.S.C. 154(b) by 278 days.

This patent is subject to a terminal disclaimer.

(21) Appl. No.: 10/731,255

(22) Filed: Dec. 9, 2003

(65) Prior Publication Data

US 2004/0138444 A1    Jul. 15, 2004

Related U.S. Application Data

(63) Continuation of application No. 10/023,077, filed on Dec. 13, 2001, now Pat. No. 6,720,418, which is a continuation of application No. 09/378,673, filed on Aug. 20, 1999, now Pat. No. 6,380,379.

(51) Int. Cl.
 C08B 31/00 (2006.01)
 C08B 30/18 (2006.01)
 C08B 37/16 (2006.01)

(52) U.S. Cl. ............ 536/45; 536/55.3; 536/102; 536/104; 536/105; 536/123.1; 536/124; 536/46; 536/103

(58) Field of Classification Search .............. 536/45, 536/55.3, 102, 104, 105, 123.1, 124, 46, 536/103
See application file for complete search history.

(56) References Cited

U.S. PATENT DOCUMENTS

| | | | |
|---|---|---|---|
| 2,280,975 | A | 4/1942 | Power et al. |
| 3,639,389 | A | 2/1972 | Hull et al. |
| 3,890,300 | A | 6/1975 | Huchette et al. |
| 4,845,208 | A | 7/1989 | Fuertes et al. |
| 4,985,553 | A | 1/1991 | Fuertes et al. |
| 5,109,128 | A | 4/1992 | Schumacher et al. |
| 5,772,013 | A | 6/1998 | Kunz et al. |
| 5,780,620 | A | 7/1998 | Mandai et al. |
| 6,380,379 | B1 * | 4/2002 | Antrim et al. ............ 536/45 |
| 6,613,898 | B1 | 9/2003 | Barresi et al. |
| 6,720,418 | B1 * | 4/2004 | Antrim et al. ............ 536/45 |

FOREIGN PATENT DOCUMENTS

| | | |
|---|---|---|
| EP | 0142725 | 8/1987 |
| EP | 0727485 | 8/1996 |
| EP | 0548399 | 9/1996 |
| WO | WO 92/18542 | 10/1992 |
| WO | WO 95/07303 | 3/1995 |
| WO | WO 97/34861 | 9/1997 |

OTHER PUBLICATIONS

Knapp., Handbook of analytical derivitazation reactions, p. 582-584, 1979.
Kearsley et al., Starch, vol. 32(80), pp. 244-247, 1980.
Bendlak, "Nuclear Magnetic Resonance Spectroscopy of Peracetylated Oligosasccharides Having 13C-Labeled Carbonyl Groups in Lieu of Permethylation Analysis for Establishing Linkage Substitutions of Sugars," Carbohydrate Research, 315, pp. 206-221 (Feb. 28, 1999).
McNeil, "Elimination of Internal Glycosyl Residues During Chemical Ionlzation-Mass Spectrometry of Per-O-Alkylated Oligosaccharide-Alditols," Carbohydrate Research, 123, pp. 31-40 (1983).
International Search Report for PCT/US00/40687 mailed Mar. 26, 2001.

* cited by examiner

Primary Examiner—Shaojia Anna Jiang
Assistant Examiner—Devesh Khare
(74) Attorney, Agent, or Firm—Banner & Witcoff, Ltd

(57) ABSTRACT

Disclosed are derivatized malto-oligosaccharides and methods for the preparation thereof. In accordance with the disclosed invention, a malto-oligosaccharide is hydrogenated to thereby obtain a hydrogenated malto-oligosaccharide, and the resulting hydrogenated malto-oligosaccharide is derivatized, such as via oxidation, esterification, etherification, or enzymatic modification. The derivatization of such hydrogenated malto-oligosaccharides results in a surprisingly low level of a formation of by-products and products of degradation. In a particularly preferred embodiment of the invention, a mixture of malto-oligosaccharides is catalytically hydrogenated under reaction conditions suitable to substantially preserve the degree of polymerization (DP) profile of the mixture. The resulting malto-oligosaccharide mixture then is derivatized to form a derivatized malto-oligosaccharide mixture.

46 Claims, No Drawings

DERIVATIZED REDUCED MALTO-OLIGOSACCHARIDES

"This application is a continuation of U.S. patent application Ser. No. 10/023,077, filed Dec. 13, 2001, (now, U.S. Pat. No. 6,720,418, issued Apr. 13, 2004, which is a continuation of Ser. No. 09/378,673, filed Aug. 20, 1999 (now, U.S. Pat. No. 6,380,379, issued Apr. 30, 2002. All parent applications are incorporated herein by reference in their entireties."

TECHNICAL FIELD OF THE INVENTION

The present invention is directed towards malto-oligosaccharide derivatives, and towards methods for the preparation thereof. More specifically, the invention is directed in its preferred embodiments towards malto-oligosaccharides that have been derivatized by oxidation, etherification, esterification, or enzymatic modification.

BACKGROUND OF THE INVENTION

Oligosaccharides are commonly prepared by the controlled hydrolytic cleavage of starches. In the production of such oligosaccharides, the glycosidic linkages of the starch molecules are partially hydrolyzed to yield at least one oligosaccharide species, and more typically, a mixture of oligosaccharides species. Oligosaccharide mixtures so prepared typically include at least one malto-oligosaccharide species. Malto-oligosaccharides are characterized as having a saccharide backbone that comprises predominantly 1–4 glycoside linkages.

Malto-oligosaccharides comprise a commercially important class of carbohydrates that fall within the general class of reducing carbohydrates, which are carbohydrates that include an acetal group that is in equilibrium with its respective aldehyde or ketone. Such malto-oligosaccharides find numerous commercial applications. Derivatized malto-oligosaccharides also are known in the art. Such derivatized malto-oligosaccharides also have many commercial uses, including, for example, encapsulants, acidulants, flocculants, adhesives, antiredeposition agents, detergent builders, and so forth.

The prior art has provided numerous processes for the derivatization of malto-oligosaccharides. Known processes are conventional and typically comprise derivatizing the malto-oligosaccharide via a conventional derivatizing process to form a derivatized product. Such prior art processes suffer from a number of drawbacks, however. For example, when subjected to certain reaction conditions, such as alkaline conditions, malto-oligosaccharides can degrade and/or undergo numerous side reactions to form respectively undesired products of degradation or reaction by-products. Such by-products and products of degradation lead to poor reaction yields, undesired color formation, and difficulties in purifying the desired derivatized malto-oligosaccharides.

It is believed that the so-called "alkaline peeling reaction," in which the reducing end sugar of a malto-oligosaccharide degrades into smaller molecules, contributes substantially to degradation and by-product formation in the derivatization of malto-oligosaccharides. In recognition of this alkaline peeling reaction, the prior art has taught in other contexts to convert a base saccharide to a glycoside, to thereby incorporate a protecting group. For example, it is known to incorporate a methyl protecting group at the reducing end of glucose to thereby form the alkaline-stable methyl glycoside. Another approach used in the prior art is the use of non-reducing sugars such as sucrose and trehalose as protecting groups. For example, U.S. Pat. No. 5,780,620 (Mandai et al.) purports to disclose non-reducing oligosaccharides wherein one or several glucosyl groups are bound to both glucosyl groups in trehalose. While the use of protecting groups such as sucrose or trehalose in connection with the preparation of a glycoside may afford an alkaline-stable product, the process of preparing such stabilized malto-oligosaccharides can be laborious and not economically attractive.

It is a general object of the present invention to provide a method for derivatizing a malto-oligosaccharide. In accordance with preferred embodiments of the invention, by-product formation and formation of products of degradation are mitigated as compared with products formed by known malto-oligosaccharide derivatization reactions. It is also a general object of the invention to provide a derivatized malto-oligosaccharide product.

THE INVENTION

The invention is premised upon the surprising discovery that reduced malto-oligosaccharides not only are alkaline-stable with respect to unmodified malto-oligosaccharides, but also may be derivatized to form derivatized malto-oligosaccharides with a surprising decrease in by-products and products of degradation, and further providing other unexpected benefits, including improved yields and improved ease of purification. Further surprising in conjunction with the derivatization of a mixture of malto-oligosaccharides is the discovery that the change in DP profile of the mixture upon oxidation, and, it is believed, other derivatization, is smaller in conjunction with reduced malto-oligosaccharides as compared with unmodified malto-oligosaccharides. Thus, not only does the derivatization of reduced malto-oligosaccharides generally result in relatively less formation of by-products and products of degradation, relatively increased yield, and ease of purification with regards to unmodified malto-oligosaccharides, the DP profile of the derivatized malto-oligosaccharide mixture generally will be relatively closer to that of the starting mixture.

In accordance with the invention, a method for preparing a derivatized malto-oligosaccharide is provided. Generally, the method comprises the steps of providing a hydrogenated malto-oligosaccharide, and derivatizing the hydrogenated malto-oligosaccharide to thereby form a derivatized malto-oligosaccharide. The malto-oligosaccharide may be obtained via the steps of providing the malto-oligosaccharide and hydrogenating the malto-oligosaccharide to thereby obtain a hydrogenated malto-oligosaccharide. Derivatized malto-oligosaccharides prepared in accordance with the method of the invention also fall within the scope of the invention. The scope of derivatization encompassed by the invention is not contemplated to be limited, and thus, for example, the hydrogenated malto-oligosaccharides may be derivatized via oxidation, esterification, etherification, or other suitable derivatization reaction. The hydrogenated malto-oligosaccharide also may be modified enzymatically to yield enzymatically modified malto-oligosaccharides.

In a particularly preferred embodiment of the invention, a mixture of hydrogenated malto-oligosaccharide is derivatized. Most preferably, the mixture is obtained via the hydrogenation of a mixture of malto-oligosaccharides under reaction conditions suitable to substantially preserve the DP profile of the reaction mixture, as taught in co-pending application Serial No. PCT/US99/01098.

DESCRIPTION OF PREFERRED EMBODIMENTS

The method of the invention is generally contemplated to be applicable to any malto-oligosaccharides species or mixture of a plurality of malto-oligosaccharides species. By "malto-oligosaccharide" is contemplated any species comprised of plural saccharide units linked predominately via 1–4 linkages, thus including, for example, maltodextrins and syrup solids. In preferred embodiments of the invention, at least 50% of the saccharide units in the malto-oligosaccharide are linked via 1–4 linkages. More preferably, at least about 60% saccharide units are linked via 1–4 linkages; even more preferably, at least about 80% of the saccharide units are so linked. Malto-oligosaccharides are contemplated to include saccharides species having an odd DP value, such as maltotriose.

Malto-oligosaccharides may be characterized by their degree of polymerization (DP), which refers to the number of saccharide monomer units in each molecule. Each malto-oligosaccharide saccharide species also may be characterized by its dextrose equivalent value (DE), which generally indicates the proportion of aldehyde, hemiacetal, or ketone groups in the molecule. Malto-oligosaccharides having a DE less than 20 prior to hydrogenation are known as maltodextrins, whereas malto-oligosaccharides having a DE of 20 or greater are known as syrup solids. The invention is contemplated to find particular applicability in connection with the derivatization of mixtures of a plurality of malto-oligosaccharides species. The malto-oligosaccharides species in the mixture may be different at least in DP value, thus defining a DP profile for the mixtures. The DP profile may be partially defined by a saccharides species having a DP value of 1, for example, dextrose or sorbitol. The mixture further may include other saccharides species or other components.

Preferably, in conjunction with the derivatization of a mixture of malto-oligosaccharides, at least a portion of the malto-oligosaccharides species in the mixture has a DP value greater than 5, and more preferably, at least one of the malto-oligosaccharides species in the mixture has a DP value of 8 or more. More preferably, at least one species has a DP value of at least 10. For example, in preferred embodiments of the invention, at least 80% of the malto-oligosaccharides species in the mixture have a DP greater than 5, and at least 60% may have a DP greater than 8. In another embodiment, at least 80% of the malto-oligosaccharides species have a DP greater than 10. In some embodiments of the invention, the DP profile of the malto-oligosaccharides mixture is such that at least 75% of the malto-oligosaccharides species in the mixture have a DP greater than 5 and at least 40% species in the mixture have a DP greater than 10. Such starting materials may be obtained conventionally, for example, by the partial hydrolysis of starch.

Suitable malto-oligosaccharides are sold as malto-dextrins under the trademark MALTRIN® by Grain Processing Corporation of Muscatine, Iowa. The MALTRIN® malto-dextrins are malto-oligosaccharide products, each product having a known typical DP profile. Suitable MALTRIN® malto-dextrins that may be derivatized in accordance with the present invention include, for example, MALTRIN® M040, MALTRIN® M050, MALTRIN® M100, MALTRIN® M150, and MALTRIN® M180. Typical approximate DP profiles for the subject MALTRIN maltodextrins are set forth in the following table (the DP profiles being approximate as indicated in the table):

|            | Typical DP profile (% dry solids basis) | | | | |
| ---------- | ------------ | ------------ | ------------ | ------------ | ------------ |
| DP profile | M180         | M150         | M100         | M050         | M040         |
| DP > 8     | 46.6 ± 4%    | 54.7 ± 4%    | 67.8 ± 4%    | 90.6 ± 4%    | 88.5 ± 4%    |
| DP 8       | 3.9 ± 2%     | 4.8 ± 1.5%   | 4.5 ± 1.5%   | 1.5 ± 1%     | 2.0 ± 1%     |
| DP 7       | 9.5 ± 2%     | 9.1 ± 1.5%   | 7.0 ± 1.5%   | 1.5 ± 1%     | 2.4 ± 1%     |
| DP 6       | 11.4 ± 2%    | 8.4 ± 1.5%   | 6.1 ± 1.5%   | 1.4 ± 1%     | 1.8 ± 1%     |
| DP 5       | 5.9 ± 2%     | 4.7 ± 1.5%   | 3.3 ± 1.5%   | 1.3 ± 1%     | 1.3 ± 1%     |
| DP 4       | 6.4 ± 2%     | 5.5 ± 1.5%   | 3.7 ± 1.5%   | 1.1 ± 1%     | 1.4 ± 1%     |
| DP 3       | 8.3 ± 2%     | 6.7 ± 1.5%   | 4.2 ± 1.5%   | 1.0 ± 1%     | 1.4 ± 1%     |
| DP 2       | 6.2 ± 2%     | 4.8 ± 1%     | 2.5 ± 1%     | 0.8* ± 1%    | 0.9* ± 1%    |
| DP 1       | 1.8 ± 1.5%   | 1.3 ± 1%     | 0.7* ± 1%    | 0.8* ± 1%    | 0.3* ± 1%    |

*MINIMUM VALUE = 0%

The invention encompasses the derivatization of malto-dextrin starting materials that have substantially the foregoing approximate DP profiles, however made. Other malto-oligosaccharides suitable for use in conjunction with the invention include other malto-dextrins, such as MALTRIN® M440, MALTRIN® M510, MALTRIN® M550, MALTRIN® M580, MALTRIN® M700, as well as corn syrup solids such as MALTRIN® M200 and MALTRIN® M250 (these having a DE>25 prior to hydrogenation). The invention is not limited to derivatization of the foregoing malto-oligosaccharides species or mixtures, and indeed, any suitable malto-oligosaccharide may be derivatized in conjunction with the invention.

Most preferably, the mixture of malto-oligosaccharides is catalytically hydrogenated to thereby substantially reduce the malto-oligosaccharides in the mixture, in some cases to a DE of essentially zero, as set forth in more detail in co-pending application serial No. PCT/US98/01098 (published as WO 99/36442). By "substantially reduced" is meant that the DE of the malto-oligosaccharide is reduced by at least about 85%, and preferably at least about 90%, relative to the initial DE thereof. The term "essentially zero" as used herein with respect to DE value refers to hydrogenated product having a DE of less than about 1. Further details concerning catalytic hydrogenation of malto-oligosaccharide mixtures are set forth in the aforementioned co-pending application serial No. PCT/US98/01098.

While is not intended to limit the invention to a particular theory of operation, it is believed that the reducing end group at the leading C-1 position of the malto-oligosaccharide aldose is generally the most reactive group on the molecule. When an unmodified malto-oligosaccharide is derivatized, for example, by oxidation, it is believed that oxidation will occur first at this position, followed by oxidation at the primary alcohol (C-6) positions on the molecule. Because the rate of the reaction is higher at the C-1 reducing end group, alternative degradation mechanisms may occur by the time the C-6 alcohols are oxidized. When the reducing end group is hydrogenated to form the corresponding alditol, however, this phenomenon is mitigated against. All of the primary alcohol groups on the malto-oligosaccharides molecule will oxidize at similar rates, thus limiting the amount of by-product formation. As the degree of polymerization of the malto-oligosaccharides increases, the number of C-6 groups increases relative to the single leading C-1 group on the malto-oligosaccharide molecule, thus leading to proportionally greater benefits.

In accordance with the invention, the malto-oligosaccharide is derivatized, by which generally is contemplated incorporating one or more substituents or chemical modifications in one or more positions on one or more saccharide units in the malto-oligosaccharide molecule. The extent of the derivatization can be expressed via the degree of substitution (DS) of the malto-oligosaccharide. In conjunction with the invention, it is possible to derivatize the malto-oligosaccharide to a DS of greater than or equal to 0.25, even more preferably, a DS of about 0.5 and even more preferably, a DS greater than about 0.8. Where applicable, the extent of derivatization may be expressed in terms of molar substitution ("MS"), for example, in the case of hydroxyalkylation. The extent of derivatization may be adjusted to the degree desired for a given application. Surprisingly, it has been found that the use of hydrogenated malto-oligosaccharides often affords a product that has a higher DS than that which would be obtained via derivatization of an unmodified malto-oligosaccharide under similar reaction conditions. The invention is applicable to the derivatization of mixtures of malto-oligosaccharides, wherein at least a portion of the malto-oligosaccharides in the mixture are derivatized. By "at least a portion" is contemplated any portion of the malto-oligosaccharides, including without limitation the derivatization of some or all malto-oligosaccharides of a given DP value.

While the invention is applicable to any derivatization via any substituent, the invention finds particular applicability to those derivatization chemistries that employ alkaline conditions. Particularly suitable derivatizations include oxidations, etherifications, and esterifications. The invention is also applicable to enzymatic modifications of the malto-oligosaccharide, which enzymatic modifications may result in an oxidized, etherified, esterified or otherwise derivatized or modified malto-oligosaccharide. Generally, any reaction conditions that will result in a derivatized malto-oligosaccharide, except possibly highly acidic conditions that might allow for hydrolysis of glycosidic linkages, may be employed. The malto-oligosaccharide preferably is derivatized in aqueous solution at a pH greater than about 6.0, and more preferably under alkaline conditions (i.e., a pH grater than 7.0).

For example, with respect to derivatization the oxidation of the malto-oligosaccharide in one or more primary alcohol positions to form carboxylic acids, a variety of oxidation reactions are known in the art and are applicable for use in conjunction with the invention. Suitable oxidizing reactants include nitroxyl radicals, nitrogen dioxide and tetroxide, and hydrogen peroxide. Alternatively, the oxidation may also be effectuated enzymatically or via electrolytic methods. Suitable such reactions are disclosed in Arts et al., *Synthesis* 1997 (6): 597–613; Roper, in *Carbohydrates As Organic Raw Materials*, Ch. 13: 267–288 (1991); and in published International Application No. WO 95/07303.

In accordance with a preferred embodiment of the invention, the malto-oligosaccharide is oxidized in the presence of a metal catalyst, such as platinum or palladium. The oxidation of glucose using palladium on carbon doped with bismuth has been described in EP 142,725 and in U.S. Pat. No. 4,845,208, and the oxidation of starch hydrolysates has been disclosed in U.S. Pat. No. 4,985,553 and in published International Application No. WO 97/34861. Platinum is preferred over palladium for oxidizing alcohol groups, inasmuch as platinum is less prone to deactivation by oxygen. However, platinum-catalyzed oxidation of dextrose to yield glucaric acid traditionally has been plagued with high levels of by-product formation, In EP 775,709, a method of combining noble metal catalysis with an electrodialysis separation is disclosed. Other oxidations known in the art include those disclosed in Glattfeld and Gershon, *J. Am. Chem. Soc.* 60:2013 (1938); Heynes and Paulsen, *Ang. Chem.* 69:600 (1957); Heynes and Beck, *Chem. Ber.* 91:1720 (1958); U.S. Pat. No. 5,109,128; EP 548,339. WO 95/07303 (use of 2,2,6,6,-tetramethylpiperdine 1-oxyl in conjunction with an oxidant system that includes sodium bromide and sodium hypochlorite to oxidize carbohydrates selectively at the C-6 position at pH's ranging from 9.8 to 11.5), and WO 92/18542 (alkaline oxidation in the present of metal ions in molecular oxygen, and a polydentate and amine ligand).

The invention also is contemplated to be applicable to etherification of malto-oligosaccharides. Preferred etherification reactions include ethoxylations, propoxylations, and similar alkoxylations, as well as reactions to introduce a cationic charge by using reagents such as 3-chloro-2-hydroxypropyl-trimethyl ammonium chloride or like reagents. Any suitable reagents in reaction conditions as are known or as may be found to be suitable may be used in conjunction with the invention. For example, reagents such as octyl bromide, allyl bromide, propylene oxide, ethylene oxide, and like chemicals conventionally used in connection with ether formation may be employed, as well as higher molecular weight polymers conventionally used in epoxide ring opening or nucleophilic displacement reactions, such as glycidyl ethers, and so forth. The etherification reaction may comprise combining the malto-oligosaccharide and alkylene oxide in any amount effective to achieve derivatization. In one embodiment, the alkylene oxide is present in an amount greater than 40% by weight of the malto-oligosaccharides starting material, such as an amount greater than 45% by weight of the malto-oligosaccharide starting material. The reaction conditions may be any conditions suitable to form a malto-oligosaccharide-alkyl ether.

Another example of the derivatization of a malto-oligosaccharide is via esterification. The esterification reaction preferably incorporates any acyl group having from 2 to 20 carbon atoms. The acyl group may be added via conventional means, such as using an acid chloride or acid anhydryde, or by such other means as may be found to be suitable. The malto-oligosaccharide may be esterified to form an acetate, benzoate, octenylsuccinate, or other suitable ester. A common esterification reaction in which a hydrogenated malto-oligosaccharide would be advantageous is an octenyl-succinylation reaction, such as that disclosed in U.S. Pat. No. 5,720,978.

The malto-oligosaccharide also may be derivatized via enzymatic modification. Any suitable enzyme as may be known or may be found to be suitable may be used in conjunction with the invention to modify the malto-oligosaccharide. It is contemplated that the enzymatic modification may result in a malto-oligosaccharide that is oxidized, esterified, or otherwise derivatized or modified. The term "derivatized" in conjunction with an enzymatically modified malto-oligosaccharide is intended to encompass such modifications as may be effected by the enzymatic modification.

The following non-limiting Examples are provided to illustrate preferred embodiments of the present invention.

EXAMPLES

Example 1

Oxidation of Malto-Oligosaccharide

In 651 ml of deionized water was slurried 1.79 grams 10% platinum on graphite (Johnson Matthey type B101026-10). The slurry was heated to 60° C. while purging with nitrogen (1.5 L/min). Once the slurry reached temperature, 14.7 grams hydrogenated MALTRIN® M180 was added. The nitrogen flow was replaced with 0.2 L/min oxygen. The reaction pH was controlled at pH 9.0 with 0.5M NaOH. Once 0.25 equivalents of NaOH was consumed (5 hours), the oxygen flow was terminated and the sample was diluted to 2 liters, then vacuum filtered through #3 Whatman filter paper, frozen, and freeze dried. The samples were analyzed for ash and for carboxyl degree of substitution via a conventional titrametric process. MALDI (matrix-assisted laser desorption ionization) mass spectra was obtained.

As a control, 14.8 grams unmodified MALTRIN® M180 was oxidized under similar reaction conditions. After 5 hours and 49 minutes, 0.127 equivalents of NaOH was found to have been consumed. The following results were obtained:

| Analysis | Example 1 | Control |
|---|---|---|
| Ash | 2.18 | 6.83 |
| DS | 0.206 | 0.322 |

The degree of substitution was higher for the control because the uncontrolled oxidation reaction created more carboxyl groups as degradation products.

The color of the product of Example 1 was significantly less than that of the control. The mass spectra indicated a significant drop in the overall molecular weight and DP profile of both of the oxidized samples, but a significantly greater preservation of molecular weight with the product of Example 1, with the maximum observed peak given as 4241 daltons for example 1, and 3276 daltons for the control.

Example 2

Propoxylation of Malto-Oligosaccharide

In a 500 ml reaction flask, which was equipped with a magnetic stirrer, a temperature control, and a condenser, 200 grams hydrogenated maltodextrin (MALTRIN® M180) was dissolved in 60 grams deionized water. To this solution was added 5.6 grams potassium hydroxide and 62.8 grams propylene oxide. The reaction mixture was refluxed for 16 hours, and allowed to heat to 65° C. Once the reaction reached temperature, it was terminated with the addition of 7 grams sodium bisulfite. The final reaction mixture had an orange color. The reaction mixture was ion-exchanged on a dual column system of 150 ml DOWEX® MONOSPHERE 66 (hydroxide form) and 150 ml DOWEX® MONOSPHERE 88 (hydrogen form), and then freeze dried to give a white product.

As a control, 140 grams MALTRIN® M180 was similarly propoxylated. The reaction mixture was a dark orange to brown color after termination with sodium bisulfite. After ion exchanging and freeze drying, the given product had a yellow color.

Each product was evaluated for hydroxypropyl degree of substitution via a conventional technique. The following results were obtained:

| | Sample Molecular Weight | | | | |
|---|---|---|---|---|---|
| Degree of Polymerization (DP) Units | MALTRIN® M180 | Example 1 (Derivatized Hydrogenated MALTRIN® M180) | | Control (Derivatized MALTRIN® M180) | |
| | | Major Peak | Minor Peak | Major Peak | Minor Peak |
| 3 | 530 | 565 | 545 | 527 | 549 |
| 4 | 690 | 727 | 692 | 689 | 728 |
| 5 | 851 | 890 | 853 | 851 | 891 |
| 6 | 1013 | 1052 | 1014 | 1013 | 1052 |
| 7 | 1175 | 1214 | 1176 | 1175 | 1214 |
| 8 | 1337 | 1376 | 1337 | 1339 | — |
| 9 | 1498 | 1499 | 1538 | 1501 | — |
| 10 | 1660 | 1660 | 1700 | 1662 | — |
| 12 | 1985 | 1984 | 2021 | 1988 | — |
| 14 | 2308 | 2308 | 2346 | 2310 | — |
| 16 | 2632 | 2630 | 2669 | 2632 | — |
| 18 | 2955 | 2954 | 2992 | 2954 | — |
| 20 | 3281 | 3277 | — | 3276 | — |
| 26 | 4244 | 4241 | — | — | — |
| 41 | 6678 | — | — | — | — |

| Analysis | Example 2 | Control 2 |
|----------|-----------|-----------|
| DS       | 0.93      | .46       |

The color of the control was significantly greater than the product of Example 2. No significant difference in maximum molecular weight was observed. The propoxylation reaction of the present invention thus yielded a product having significantly less color and higher DS as compared with the control.

Example 3

Carboxymethylation of Malto-Oligosaccharide

Fifty grams of hydrogenated MALTRIN® M100 was dissolved in 100 ml water. Monochloroacetic acid (0.5 equivalents) was added, followed by 24.2 grams of 50% NaOH (1.0 equivalent) The mixture was heated to 70° C. and held at this temperature for 2 hours. After 2 hours, the pH was measured and found to be 11.2, after which the pH was adjusted to a final pH of 8.0 with the addition of 6N HCl. The reaction contents were cooled and then slowly poured into 2000 liters methanol to precipitate a beige-colored solid. The solid was washed with a second 200 ml aliquot of methanol and dried under vacuum for 2 days to yield 58.1 grams of a product which contained 13.4% moisture and 5.75 ash. The ash-moisture-corrected theoretical yield of the product was 85%. The DS was determined via a conventional titrametric process and was found to be 0.30. MALDI molecular weight analysis demonstrated a maximum molecular weight of 2241 daltons and strong evidence of mono-, di- and tri-substituted carboxymethylation of the malto-oligosaccharide molecules.

As a control, 50 grams of MALTRIN® M100 was carboxymethylated in a similar reaction. After the initial reaction mixture had been held for 2 hours, the reaction pH was found to be 8.0. The precipitated solid was dark yellow, and the dry solid yield was 35.3 grams product which contained 11.2 percent moisture and 4% ash. The ash- and moisture-corrected theoretical yield was 54%, and the DS was found to be 0.22. The maximum molecular weight was found to be 1236 daltons, and the mass spectra analysis gave some evidence only for mono-substitution. The control had significantly more color than the product of Example 3. This Example illustrates that a higher DS, better recovery, better preservation of molecular weight, and better color were obtained with hydrogenated malto-oligosaccharides in accordance with the invention than the control.

Example 4

Hydroxypropyl Trimethylammonium Chloride

Derivatization of Malto-Oligosaccharide

Two hundred grams (dry solid basis) of hydrogenated MALTRIN® M100 was dissolved in 280 ml water. To this solution was added 24.0 grams of a 50% solution (0.24 equivalents) sodium hydroxide over a period of 10 minutes. QUAB 151 (2,3 epoxypropyl-n,n,-trimethylammonium chloride, DeGussa Corp.) 214.0 grams of a 70% solution (0.8 equivalents) was added to the reaction and the temperature was maintained at 60° C. for three hours. After three hours the reaction mixture was a rusty brown color. The solution was pH-adjusted to 6.0 with HCl and freeze dried to yield 340 grams of a light brown solid. The unpurified, recovered yield after moisture and ash correction was 88%. MALDI molecular weight analysis indicated a maximum molecular weight about 1603 daltons.

As a control, 200 grams unmodified MALTRIN® M100 was similarly derivatized. After three hours, the reaction mixture was found to be black and viscous. The purified, recovered yield was 92%, but MALDI molecular weight analysis indicated a maximum molecular weight of about 1330 daltons. The control had significantly more color than the Example. Both the products of Example 1 and of the control were substituted to about the same extent, as evidenced by nitrogen combustion analysis. Thus, the Example provided a product with less color, and better preservation of molecular weight than the control.

All of the foregoing examples illustrate that an improved product, with improved ease of purification (as evidenced by the lower color levels), may be obtained using hydrogenated malto-oligosaccharides.

Example 5

Enzymatic Modification of Malto-Oligosaccharide

Hydrogenated MALTRIN® M180, 50 g, is dissolved in 25 g of water and pH controlled at 7.0. Vinyl acetate, 5 g, is poured into the reaction mixture and the system stirred vigorously. Porcine pancreatic lipase, 5 g, is added and the reaction is stirred for 24 hours at ambient temperature. The resulting maltodextrin is isolated by precipitation by ethanol, and dried to yield a partially acetylated product.

While particular embodiments of the invention have been shown, it should be understood that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention. All references and cited herein are hereby incorporated by reference in their entireties. The disclosure of co-pending application serial No. PCT/US98/01098 also is hereby incorporated by reference in its entirety.

What is claimed is:

1. A method for preparing a mixture of derivatized malto-oligosaccharide species, comprising the steps of:
   providing a mixture of a plurality of malto-oligosaccharide species;
   catalytically hydrogenating said mixture under hydrogenation conditions suitable to substantially preserve the DP (degree of polymerization) 1-8 profile of said mixture to thereby obtain a hydrogenated malto-oligosaccharide mixture, wherein said mixture is hydrogenated to a DE (dextrose equivalent) of essentially zero, and
   derivatizing said hydrogenated malto-oligosaccharide mixture by introducing a charged species, to thereby form a derivatized malto-oligosaccharide mixture.

2. A method according to claim 1, said derivatizing comprising etherfying said hydrogenated malto-oligosaccharide mixture to thereby introduce a charged species.

3. A method according to claim 2, said derivatizing comprising etherfying said hydrogenated malto-oligosaccharide mixture to introduce a cationic charge.

4. A method according to claim 2, wherein said hydrogenated malto-oligosaccharide mixture comprises a maltodextrin.

5. A method according to claim 4, wherein at least 40% of the malto-oligosaccharide species in the mixture have a DP greater than 10.

6. A method according to claim 2, wherein the derivatized malto-oligosaccharide mixture has a degree of substitution of 0.25 or more.

7. A method according to claim 3, whereby said cationic charge is introduced by derivatizing with an amino compound.

8. A method according to claim 7, wherein said amino compound is a tertiary or quaternary amine.

9. A method according to claim 8, said hydrogenated malto-oligosaccharide mixture being derivatized with 3-chloro-2-hydroxypropyl-trimethyl ammonium chloride.

10. A method according to claim 9, wherein said hydrogenated malto-oligosaccharide mixture comprises a maltodextrin.

11. A method according to claim 10, wherein at least 40% of the malto-oligosaccharide species in the mixture have a DP greater than 10.

12. The derivatized, charged malto-oligosaccharide mixture produced by the method of claim 9.

13. A mixture of derivatized malto-oligosaccharide species prepared by a method comprising the steps of:
provideing a mixture of a plurality of malto-oligosaccharide species;
catalytically hydrogenating said mixture under hydrogenation conditions suitable to substantially preserve the DP1-8 profile of said mixture to thereby obtain a hydrogenated malto-oligosaccharide mixture, wherein at least 40% of the malto-oligosaccharide species in the mixture have a DP greater than 10, and said mixture is hydrogenated to a DP of essentially zero; and
derivatizing said hydrogenated malto-oligosaccharide mixture by introducing a charged species, to thereby form a derivatized malto-oligosaccharide mixture.

14. A mixture according to claim 13, said derivatizing comprising etherfying said hydrogenated malto-oligosaccharide mixture to thereby introduce a charged species.

15. A mixture according to claim 14, said derivatizing comprising etherfying said hydrogenated malto-oligosaccharide mixture to introduce a cationic charge.

16. A mixture according to claim 14, wherein said hydrogenated malto-oligosaccharide mixture comprises a maltodextrin.

17. A mixture according to claim 16, wherein at least 40% of the malto-oligosaccharide species in the mixture have a DP greater than 10.

18. A mixture according to claim 14, wherein the derivatized malto-oligosaccharide mixture has a degree of substitution of 0.25 or more.

19. A mixture according to claim 15, whereby said cationic charge is introduced by derivatizing with an amino compound.

20. A mixture according to claim 19, wherein said amino compound is a tertiary or quaternary amine.

21. A mixture according to claim 20, said hydrogenated malto-oligosaccharide mixture being derivatized with 3-chloro-2-hydroxypropyl-trimethyl ammonium chloride.

22. A method according to claim 21, wherein said hydrogenated malto-oligosaccharide mixture comprises a maltodextrin.

23. A method according to claim 22, wherein at least 40% of the malto-oligosaccharide species in the mixture have a DP greater than 10.

24. A method for preparing a mixture of derivatized malto-oligosaccharides comprising:
providing a mixture of malto-oligosaccharides, such mixture having been prepared by catalytically hydrogenating a mixture of malto-oligosaccharides under conditions suitable to substantially preserve the DP1-8 profile of said mixture; and derivatizing said hydrogenated malto-oligosaccharide mixture by introducing a charged species, to thereby form a derivatized charged malto-oligosaccharide mixture.

25. A method according to claim 24 said derivatizing comprising etherfying said hydrogenated malto-oligosaccharide mixture to thereby introduce a charged species.

26. A method according to claim 25, said derivatizing comprising etherfying said hydrogenated malto-oligosaccharide mixture to introduce a cationic charge.

27. A method according to claim 25, wherein said hydrogenated malto-oligosaccharide mixture comprises a maltodextrin.

28. A method according to claim 27, wherein at least 40% of the malto-oligosaccharide species in the mixture have a DP greater than 10.

29. A method according to claim 25, wherein the derivatized malto-oligosaccharide mixture has a degree of substitution of 0.25 or more.

30. A method according to claim 26, whereby said cationic charge is introduced by derivatizing with an amino compound.

31. A method according to claim 30, wherein said amino compound is a tertiary or quaternary amine.

32. A method according to claim 31, said hydrogenated malto-oligosaccharide mixture being derivatized with 3-chloro-2-hydroxypropyl-trimethyl ammonium chloride.

33. A method according to claim 32, wherein said hydrogenated malto-oligosaccharide mixture comprises a maltodextrin.

34. A method according to claim 33, wherein at least 40% of the malto-oligosaccharide species in the mixture have a DP greater than 10.

35. The derivatized charged malto-oligosaccharide mixture produced by the method of claim 32.

36. A mixture of derivatized charged malto-oligosaccharides prepared by a method comprising the steps of:
providing a mixture of malto-oligosaccharides, such mixture having been prepared by catalytically hydrogenating a mixture of malto-oligosaccharides under conditions suitable to substantially preserve the DP1-8 profile of said mixture; and derivatizing sad hydrogenated malto-oligosaccharide mixture by introducing a charged species, to thereby form a derivatized charged malto-oligosaccharide mixture.

37. A mixture according to claim 36, said derivatizing comprising etherfying said hydrogenated malto-oligosaccharide mixture to thereby introduce a charged species.

38. A mixture according to claim 37, said derivatizing comprising etherfying said hydrogenated malto-oligosaccharide mixture to introduce a cationic charge.

39. A mixture according to claim 37, wherein said hydrogenated malto-oligosaccharide mixture comprises a maltodextrin.

40. A mixture according to claim 39, wherein at least 40% of the malto-oligosaccharide species in the mixture have a DP greater than 10.

41. A mixture according to claim 37, wherein the derivatized malto-oligosaccharide mixture has a degree of substitution of 0.25 or more.

42. A mixture according to claim 38, whereby said cationic charge is introduced by derivatizing with an amino compound.

43. A mixture according to claim 42 wherein said amino compound is a tertiary or quaternary amine.

44. A mixture according to claim 43, said hydrogenated malto-oligosaccharide mixture being derivatized with 3-chloro-2-hydroxypropyl-trimethyl ammonium chloride.

45. A method according to claim 44, wherein said hydrogenated malto-oligosaccharide mixture comprises a maltodextrin.

46. A method according to claim 45, wherein at least 40% of the malto-oligosaccharide species in the mixture have a DP greater than 10.

* * * * *

UNITED STATES PATENT AND TRADEMARK OFFICE
CERTIFICATE OF CORRECTION

PATENT NO.        : 7,091,335 B2  
APPLICATION NO. : 10/731255  
DATED             : August 15, 2006  
INVENTOR(S)       : Richard L. Antrim and Frank W. Barresi It is certified that error appears in the above-identified patent and that said Letters Patent is hereby corrected as shown below:

In Column 4, Line 52 delete - PCT/US98/01098, replace with PCT/US99/01098

In Column 4, Line 61 delete - PCT/US98/01098, replace with PCT/US99/01098

In Column 10, Line 44 delete - PCT/US/98/01098, replace with PCT/US99/01098

Signed and Sealed this

Twenty-second Day of December, 2009

David J. Kappos
*Director of the United States Patent and Trademark Office*